United States Patent
Zhang et al.

(10) Patent No.: US 6,797,669 B2
(45) Date of Patent: Sep. 28, 2004

(54) CATALYST FOR SELECTIVE HYDROGENATION, ITS PREPARATION PROCESS AND APPLICATION

(75) Inventors: Qianwen Zhang, Beijing (CN); Han Zhang, Beijing (CN)

(73) Assignees: China Petroleum & Chemical Corporation, Beijing (CN); Beijing Research Institute of Chemical Industry, China Petroleum & Chemical Corporation, Beijing (CN)

( * ) Notice: Subject to any disclaimer, the term of this patent is extended or adjusted under 35 U.S.C. 154(b) by 102 days.

(21) Appl. No.: 10/033,661

(22) Filed: Dec. 27, 2001

(65) Prior Publication Data

US 2002/0165092 A1 Nov. 7, 2002

(30) Foreign Application Priority Data

Dec. 29, 2000 (CN) ........................ 00136873 A
Dec. 29, 2000 (CN) ........................ 00136874 A

(51) Int. Cl.⁷ .................. B01J 23/42; B01J 23/44; B01J 23/40; B01J 23/58; B01J 23/72
(52) U.S. Cl. .................. 502/339; 502/327; 502/328; 502/330; 502/331; 502/332; 502/333; 502/350; 502/351; 502/355; 502/415; 502/439
(58) Field of Search .................. 502/327, 328, 502/330, 331, 332, 333, 339, 350, 351, 355, 415, 439

(56) References Cited

U.S. PATENT DOCUMENTS

| | | | | |
|---|---|---|---|---|
| 3,615,207 A | * | 10/1971 | Lee | 23/207 |
| 3,635,841 A | * | 1/1972 | Keith et al. | 252/466 PT |
| 4,088,607 A | * | 5/1978 | Weidenbach et al. | 252/466 PT |
| 4,992,407 A | * | 2/1991 | Chakraborty et al. | 502/327 |
| 5,559,065 A | * | 9/1996 | Lauth et al. | 502/5 |
| 5,580,838 A | * | 12/1996 | Patterson | 502/159 |
| 6,074,979 A | * | 6/2000 | Hagemeyer et al. | 502/159 |
| 6,203,771 B1 | * | 3/2001 | Lester et al. | 423/219 |
| 6,528,453 B2 | * | 3/2003 | Baker et al. | 502/325 |
| 6,534,438 B1 | * | 3/2003 | Baker et al. | 502/325 |

* cited by examiner

*Primary Examiner*—Cam N. Nguyen
(74) *Attorney, Agent, or Firm*—Birch, Stewart, Kolasch & Birch, LLP

(57) ABSTRACT

A catalyst for selective hydrogenation of alkynes and dienes, its preparation process and application. The catalyst has an inorganic oxide support, a major active component palladium, and a Group IB metal promoter. The active components are uniformly distributed in the catalyst body within the thickness between the support surface and the depth of more than 300 μm. The catalyst of the present invention has high activity, high selectivity, ability to resist sulfur and arsenic poisoning. The catalyst is particularly applicable to $C_2$–$C_3$ fraction with any concentrations of hydrogen and CO.

13 Claims, 1 Drawing Sheet

CATALYST FOR SELECTIVE HYDROGENATION, ITS PREPARATION PROCESS AND APPLICATION

FIELD OF THE INVENTION

The present invention relates to a highly active and selective catalyst for the selective hydrogenation of alkynes and dienes. The present invention also relates to the preparation process and application of the catalyst.

BACKGROUND OF THE INVENTION

It is well known that the ethylene-rich fraction contains 0.3–3% of acetylene impurity, which is a poison to the polyethylene catalyst and affects the proper proceeding of the polymerization reaction of ethylene. In order to prevent the aforesaid poisoning from taking place, catalytic selective hydrogenation is generally used to convert the acetylene in the ethylene-rich fraction to ethylene. But in the reaction of selective hydrogenation to remove acetylene, the acetylene adsorbed on the bearer surface can easily be converted into unsaturated $C_4$ hydrocarbons, such as 1,3-butadiene, etc. through oligomerization. These unsaturated $C_4$ hydrocarbons would further react with acetylene or ethylene or other unsaturated hydrocarbons to form $C_6$–$C_{24}$ oligomers, which are commonly referred as "green oil" and inevitably adhere onto the catalyst for alkyne selective hydrogenation. The adherence of the "green oil" onto the catalyst for alkyne selective hydrogenation would lead to the gradual drop of the activity and selectivity of the catalyst for selective hydrogenation and the shortening of the operation period. This would result in a frequent regeneration and shortened lifetime of the catalyst, and thereby an increase in the operation cost.

The catalyst for the selective hydrogenation of alkynes and dienes is obtained by loading a noble metal, such as palladium, on a porous inorganic material, such as disclosed in U.S. Pat. No. 4,762,956. In order to enhance the selectivity of the catalyst and alleviate the deactivation of the catalyst due to green oil formed by the oligomerization reaction during hydrogenation, a promoter such as Group IB element (e.g., Pd—Au as disclosed in U.S. Pat. No. 4,490,481; Pd—Ag as disclosed in U.S. Pat. No. 4,404,124; and Pd—Cu as disclosed in U.S. Pat. No. 3,912,789), or alkali or alkali earth metal (such as disclosed in U.S. Pat. No. 5,488,024) promoter is added. The support is alumina, silicon dioxide (such as disclosed in U.S. Pat. No. 5,856,262), or honeycomb cordierite (such as disclosed in CN 1176291), etc.

The traditional hydrogenation catalyst generally has a larger specific surface area to provide the catalyst with a sufficient activity. The depth of hydrogenation is generally controlled through controlling the amount of the introduced hydrogen and the selectivity of acetylene hydrogenation into ethylene is regulated through the addition of trace amount of CO. A concentration of CO over a certain level would cause the poisoning of the catalyst. An excessive amount of hydrogen would cause not only the hydrogenation of mono-olefins, but also too steep elevation and even "run away" of the temperature of the catalyst bed.

Therefore, the supported palladium catalyst of the prior art is not suitable for the hydrogenation of the fraction containing larger amounts of hydrogen and CO. Especially in the "front-end hydrogenation to remove acetylene" technology (that is, to remove acetylene first, then to separate methane and hydrogen), because of the high concentration of hydrogen (about 10–20 mol %) and CO (500–5000 ppm (mol)) in the reactant stream, the requirement for the activity and selectivity of the hydrogenation catalyst is even higher. In fact, the key to the improvement of the separation flow of the front-end hydrogenation acetylene is to increase the selectivity and activity of the selective hydrogenation catalyst and lower the sensitivity of the catalyst to the concentrations of hydrogen and CO.

In order to alleviate the effect of the variation in CO concentration on the activity and selectivity of the catalyst, U.S. Pat. No. 4,404,124 proposes a palladium catalyst with a very thin shell, into which silver is added as a promoter component. The patent points out that the palladium component should be distributed within 300 $\mu$m of the exterior layer of the catalyst particle and the silver component should be uniformly distributed in the catalyst. CN 95107324.9 discloses a selective hydrogenation catalyst for hydrogenating in $C_2$ or $C_3$ alkyne into the corresponding alkene, wherein at least 80% contents of Pd and IB group metal distribute within the shell constituted by the thickness of r to at least 0.8 r of the support of the alumina balls or the extrusions. It can be seen from the examples of the invention that the stability of the catalyst is elongated from 22–66 h for the catalysts in the comparative examples to 85–121 h for the catalysts in the examples according to the present invention. Even so, the catalyst still needs to regenerate every 3–4 days. Besides, the comparative reference does not mention that the catalyst can be used at high hydrogen concentrations and the hydrogenation feed stock does not contain CO, which is a poison to palladium catalysts. The comparative reference does not disclose a catalyst for selective hydrogenation which can be used at high concentrations of hydrogen and CO and has a operation lifetime over hundreds hours.

SUMMARY OF THE INVENTION

It is surprisingly discovered by the present inventors that it is possible to decrease the yield of the green oil and elongate the lifetime of the catalyst to over about 1000 h by simultaneously distributing palladium and a Group IB metal in the catalyst body in a depth more than about 300 $\mu$m from the support surface. The selectivity for alkyne and diene hydrogenation is higher than about 90%. With a space velocity of about 12000–15000 $h^{-1}$, acetylene can be removed to less than about 1 ppm, thus the activity and selectivity of the catalyst is greatly increased. The applicable range of the catalyst is wide and its catalytic performance is not affected by the variation in the concentration of CO. The content of hydrogen in the reactant stream can be about 1–30 mol % and the content of CO can be about 0–5000 ppm. The catalyst is suitable for both fore-hydrogenation and post-hydrogenation.

The present invention provides a catalyst which has low yield of "green oil", long service lifetime, and high activity and selectivity and is applicable to the selective hydrogenation of alkynes and dienes with various concentrations of hydrogen and CO.

The present invention also provides a process for preparing the catalyst of the present invention.

The present invention provides the application of the catalyst of the present invention to the selective hydrogenation of mixed components containing alkynes and dienes to convert them into the corresponding monoolefins.

Another way to raise the selectivity and activity of the catalyst for selective hydrogenation is to improve the pore structure of the support. However, since the conventional catalyst support has lots of micropores (<20 nm) and minipores (20–50 nm), there the catalyst prepared by loading an active component such as palladium on the support surface is used to hydrogenate alkynes and dienes, a lot of green oil is produced and the selectivity is low. To solve the above problems of the prior art, the support with macropores and low surface acidity is prepared generally by raising the calcination temperature, such as disclosed in U.S. Pat. No. 4,762,956. But the catalyst prepared with such a support has a low dispersion of palladium and therefore a low activity for hydrogenation.

It is surprisingly discovered by the present inventors that a macroporous support with low surface acidity can be prepared by calcining the chemical composite support of alumina and titania at lower temperatures. The support endows the catalyst with higher activity and selectivity, low yield of the green oil, and resistance to poisoning by arsenic sulfide. The operation period increases by about 0.5–1.0 time and the lifetime increases by over one time compared to the prior catalyst.

The present invention provides a support with which catalyst of high activity and selectivity for selective hydrogenation can be made. This support is particularly suitable for preparing the alkyne front-end hydrogenation catalyst.

The present invention also provides a process for preparing a catalyst support of the present invention.

The present invention provides a selective hydrogenation catalyst, which comprises:

an inorganic oxide support selected from alumina, titania, and a chemical composite of alumina and titania;

a major active component Pd of a content of about 0.002–1.0% based on the total weight of the catalyst; and one or more promoters selected from Group IB metals and the mole ratio of palladium to the Group IB metal is in range between about 1 and about 20;

wherein the major component palladium and the promoter are uniformly dispersed together in the catalyst body within a thickness between the support surface and the depth of more than about 300 μm.

The present invention provides a process for preparing the selective hydrogenation catalyst, which comprises the following steps:

preparing an inorganic oxide support, which is selected from alumina, titania, and a chemical composite of alumina and titania;

impregnating the active component, wherein the inorganic oxide support is impregnated with a mixed solution of water soluble inorganic salts of palladium and a Group IB metal to allow the active component palladium and the group IB metal promoter to be absorbed into the pores of the support together and uniformly distributed in the catalyst body within a thickness between the support surface and the depth of more than 300 μm; the inorganic salts of palladium and the Group IB metal is dissolved in deionized water to form an impregnation solution, the total amount of which equals the pore volume of the support; the pH value of the impregnation solution is adjusted to be about 1–4 to control the dispersion depth of the active component and the promoter and then the impregnated support is dried at about 80–150° C.; and decomposing the catalyst, wherein the impregnated support is decomposed in an air atmosphere at about 300–800° C. for about 2–10 h. The active component and the promoter of the catalyst exist in the form of oxides in the catalyst body within a thickness between the support surface and the depth of more than about 300 μm.

The present invention provides a process for preparing the chemical composite of alumina and titania. The process comprises the following steps: $MAlO_2$ and soluble titanium salt are dissolved in water at about 20–80° C., and then the mixture is neutralized with an MOH solution to form a co-precipitate of aluminum-titanium hydroxide, which is stirred for about 10–30 h to form uniform crystal particles. The resultant is filtered and washed away the $M^+$ and acid radical negative ions with deionized water and then the derived aluminium-titanium hydroxide is dried at about 100–150° C. After pulverizing, the solid sample is formed by kneading and then calcined at about 800–1100° C. to obtain the chemical composite support of alumina-titania, wherein the M is Na, K or Li.

Figure 1:
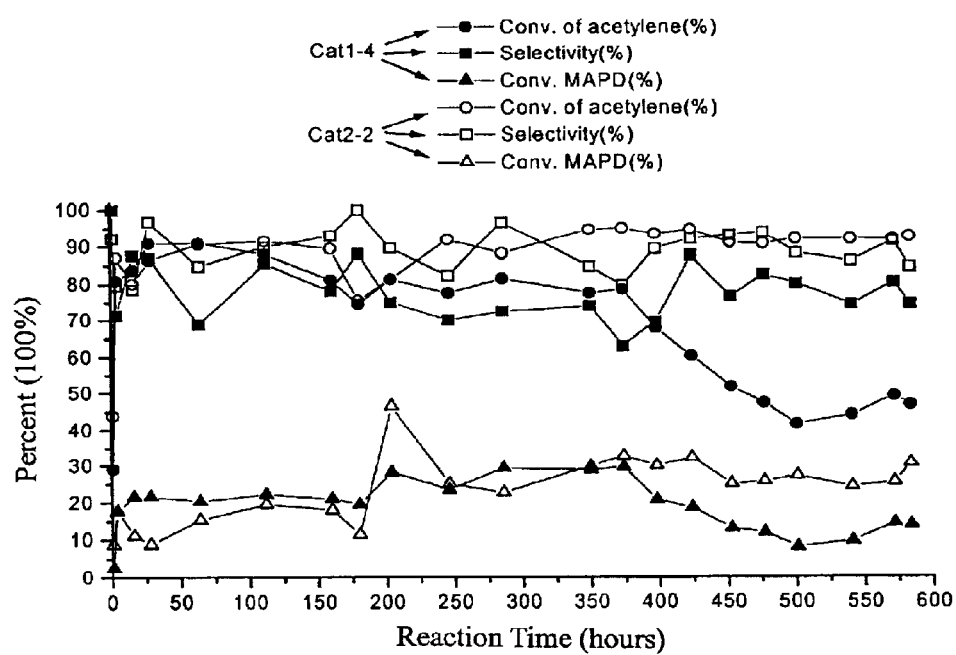
FIG. 1 shows the relation of the activity and selectivity of catalyst 1-4 and 2-2 with time on stream (TOS).

The present invention will be further described below with examples. It should be pointed out that the examples are only illustrational, and the real scope and spirit of the invention are in the claims.

DETAILED DESCRIPTION OF THE INVENTION

The present invention provides a selective hydrogenation catalyst, which can comprise:

an inorganic oxide support selected from alumina, titania, and a chemical composite of alumina and titania;

a major active component Pd of a content of about 0.002–1.0% based on the total weight of the catalyst; and one or more promoters selected from Group IB metals and the mole ratio of palladium to the Group IB metal is in range between about 1 and about 20;

wherein the major component palladium and the promoter are uniformly dispersed together in the catalyst body within a thickness between the support surface and the depth of more than about 300 μm.

The catalyst support of the present invention can comprise a chemical composite of alumina-titania. The weight percent of alumina can be about 1–99%, preferably about 10–90%, more preferably about 20–80%, and most preferably about 40–60%. The support can have the following physical properties: bulk density about 0.7–0.9 g/ml, pore volume about 0.3–0.6 ml/g, specific surface area about 10–60 m$^2$/g, mean pore diameter about 40–100 nm. The pore distribution can exhibit a doublet at about 50 nm and about 1000 nm.

The content of the major active component, palladium, can be about 0.002–1.0% based on the total weight of the catalyst, preferably about 0.005–0.5%, and most preferably about 0.01–0.05%.

The promoters of the present invention can be one or more selected from Group IB metals, such as Cu, Ag, and Au. The mole ratio between palladium and the Group IB metals can be about 1–20, preferably about 1–10, and most preferably about 1.5–5.0.

The major component palladium and the promoter can be uniformly dispersed in the catalyst body within a thickness between the support surface and the depth of more than about 300 μm, preferably about 500–1000 μm. Generally speaking, when the radius of the φ=3 support particle R is about 1.5 mm, the region where the active component is uniformly distributed is the within the portion formed between the two spherical surfaces with radiuses of r=1.5 mm and r<1.2 mm, i.e., the portion of the hollow sphere from r=R to r<0.8R. This region is at least deeper than that of the comparative reference (such as CN 95197324.9), which is formed between the two spherical surfaces with radiuses of r=R and r>0.8R. When the active component is distributed in the catalyst body within the thickness between the support surface and the depth of r=500 μm, even to r=1000 μm, its distribution region is the portion of the hollow sphere from r=R to r=0.67 R, even from r=R to r=0.3R. The catalyst of the present invention can exist as oxides in the catalyst body within a thickness between the support surface and the depth of more than about 300 μm. In the hydrogen atmosphere under reaction conditions, the major active component palladium and the promoter are reduced to fine alloy particles with diameters of about 2–10 nm.

The catalyst of the present invention can also comprise alkali metals and/or alkali earth metals. The content of such alkali metals and/or alkali earth metals can be about 0.05–20% of the total weight of the catalyst. Said alkali metal can be one or more selected from the group consisting of Li, Na, K, Rb, and Cs, preferably Li, Na, K. The alkali earth metal can be one or more selected from the group consisting of Be, Mg, Ca, Sr, and Ba, preferably Mg, Ca, and Ba.

The preparation process of the present invention can comprise three steps: preparing the support, impregnating the active component, and decomposing the catalyst.

1. Preparing the Support

The support of the present invention can be prepared by the conventional process. For example, aluminite (the major component is alumina) can be dissolved in a NaOH solution. The solution can be neutralized with a diluted solution of nitric acid to yield a $Al(OH)_3$ precipitate, which is then washed with deionized water for several times to wash away $Na^+$ and $NO_3^-$. The precipitate can be dried, formed, and calcined at a high temperature to yield the alumina support.

The chemical composite support of alumina and titania of the present invention can be prepared by the various processes. For example, $MAlO_2$ and soluble titanium salt can be dissolved in water at about 20–80° C. The mixture can be neutralized with an MOH solution to neutrality to form a co-precipitate of aluminum-titanium hydroxide, which is stirred for about 10–30 h to form uniform crystal particles. The resultant can be filtered and washed away the $M^+$ and acid radical negative ions with deionized water. The derived aluminium-titanium hydroxide can be dried at about 100–150° C. After pulverizing, the solid sample can be formed by kneading and then calcined at about 800–1100° C. to obtain the chemical composite support of alumina-titania, wherein the M is Na, K, or Li.

In a preferred embodiment of the present invention, the support of the present invention can be prepared by the following process: $NaAlO_2$ and $TiCl_4$ solutions can be mixed at about 20–80° C. (the equivalent ratio of Al to Ti can be about (10–0.5): 1). The mixture can be neutralized with a NaOH solution to form a co-precipitate of aluminum-titanium hydroxide, which is stirred for about 10–30 h to form uniform crystal particles. The resultant is filtered and washed away the $Na^+$ and $Cl^-$ ions with deionized water and then the resultant mixed hydroxide can be dried at about 100–150° C. The dry sample can be pulverized into fine powders of about 120–180 mesh and after kneading. The fine powders can be extruded into long strips of about φ3 to about φ6 mm, such as using a twin screw extruder.

After being dried at about 100–150° C., the strips can be calcined in a muffle furnace at about 500–1100° C., such as in an air atmosphere at about 800–1000° C. for about 0.5–10 h, or for about 1–3 h to yield a mixed alumina-titania support. In one embodiment, the support can have a bulk density of about 0.7–0.9 g/ml, a pore volume of about 0.3–0.6 ml/g, a specific surface area of about 10–50 $m^2/g$ (BET nitrogen method) or about 20–60 $m^2/g$ (mercury intrusion method). The pore diameter can exhibit a two peaks distribution at about about 50 nm and 1000 nm. The most probable pore diameter can be about 200–1000 nm. The mean pore diameter ($4V/A^+$) can be about 40–100 nm.

2. Impregnating the Active Component

The chemical composite support of alumina-titania can be impregnated with a mixed solution of water-soluble inorganic salts of palladium and a Group IB metal to allow the active component and the promoter to be absorbed into the pores of the support together and uniformly distributed. The inorganic salts of palladium and the Group IB metal can be dissolved in deionized water to form an impregnation solution, the total amount of which can equal the pore volume. The pH value of the impregnation solution can be adjusted to be about 1–4 to control the dispersion depth of the active component and the promoter. The impregnated support can be dried at about 80–150° C. The distribution of the active component of the catalyst is determined with SEM and the particle size is determined with TEM.

3. Decomposing the Catalyst

The supported catalyst can be decomposed in an air atmosphere at about 300–800° C., preferably about 400–500° C., for about 2–10 h. The active components of the catalyst can exist as oxides in the catalyst body within the thickness between the support surface and the depth of more than about 300 μm. In the hydrogen atmosphere under reaction conditions, the active components of the catalyst can be reduced to alloy.

When the catalyst of the present invention is applied to the selective hydrogenation of mixed components containing alkynes and dienes to convert them into mono-olefins by means of the conventional method, not only the activity, but also the selectivity is high, and the performance of the catalyst is basically not affected by the variation in CO concentration. The catalyst of the present invention is particularly suitable for the "fore-hydrogenation alkyne removal" technology of $C_2$, $C_3$, or a mixed $C_2$ and $C_3$ feed containing any amount of hydrogen and CO. The catalyst of the present invention is suitable for the reactors of the isothermal bed, adiabatic bed, etc.

The preparation process of the present invention can ensure a uniform dispersion of the major active component Pd and the Group IB metal promoter of the catalyst in the catalyst body within the thickness between the support surface and the depth of more than about 300 μm. Metal Pd and Group IB or other metals can form stable and uniform alloy particles, such as by reducing the composite oxide, which is formed at a high temperature and in oxygen atmosphere, in hydrogen atmosphere. Because of the surface tension caused by the formation of the alloy, the atoms of the Group IB metal concentrate on the surface of the alloy. The activity and selectivity of the catalyst for hydrogenation can be enhanced via a synergetic effect of palladium and the Group IB metal.

Since the active component of the catalyst of the present invention can be dispersed in the catalyst body to a sufficient depth, generally from the support surface to more than about 300 μm, the active component can have a higher dispersion, which can decrease the yield of the green oil formed from oligomers decreases. Thus, the catalyst can have a longer lifetime. According to the present invention, a higher activity of the catalyst is ensured at various concentrations of hydrogen and CO. The use of a chemical composite support of alumina-titania provided by the present invention can overcome the shortcomings of the high yield of the green oil and the low selectivity for hydrogenation when the conventional alumina support of the prior art is used in the hydrogenation (due to the large number of small and micro pores and the higher surface acidity). Thereby, the catalyst of the present invention can have a high activity and selectivity for hydrogenation, a long operation period, and resistance to sulfur and arsenic poisoning.

During the course of the application, various publications mentioned above have been referred to, the disclosures of which are all incorporated herein for reference.

EXAMPLES

Comparative Example 1

A commercial dry gel of pseudo-boehmite aluminum hydroxide was formed into small spheres with diameters of 2–4 mm. The spheres were calcined in a muffle furnace to 1400° C. at a rate of 200° C./h and maintained at this temperature for 4 h to yield the required support having a pore volume of 0.37 ml/g, a bulk density of 1.0 g/ml, a specific surface area of 4.6 $m^2$/g (BET nitrogen method) or 12.5 $m^2$/g (mercury intrusion method), a most probable pore diameter of 270 nm, and a mean pore diameter of 274 nm. 0.85 ml of palladium nitrate solution containing 4.7 mg Pd/ml, and 6.5 ml of water were added into a beaker and thoroughly mixed to prepare the impregnation solution. 20 g of the support was put into a 100 ml beaker, into which the prepared impregnation solution was added to impregnate the support. The resultant was dried at 120° C. for 8 h and decomposed in an air atmosphere at 450° C. to yield catalyst 1-1. The SEM measurement shows that 90% palladium is distributed within a shell of about 300 μm in thickness.

Comparative Example 2

In this Comparative Example, 3 ml of silver nitrate solution containing 5 mg Ag/ml, and then 4.4 ml of water were added into a beaker and thoroughly mixed to prepare the silver impregnation solution. 20 g of the support as in Comparative Example 1 was put into a 100 ml beaker, into which the prepared silver impregnation solution was added to impregnate the support. The impregnated support was dried at 120° C. for 8 h. 0.6 ml of palladium chloride solution containing 10.3 mg Pd/ml, and then 6.8 ml of water were added in a beaker, and thoroughly mixed to prepare the palladium impregnation solution. The support which had been impregnated with silver nitrate solution was added into the palladium impregnation solution to fully be impregnated. Then the wet catalyst was dried at 120° C. for 8 h and decomposed in an air atmosphere at 450° C. to yield catalyst 1-2. The SEM measurement shows that 90% palladium is distributed within a shell of about 300 μm in thickness and that silver is uniformly distributed.

Example 1

According to Example 1, about 0.6 ml of cupric nitrate containing about 10 mg Cu/ml, about 0.85 ml of palladium nitrate containing about 4.7 mg Pd/ml and about 6.8 ml of water were added into a beaker and thoroughly mixed. The pH value of the solution was adjusted to pH=1.2 with, such as nitric acid and ammonia, to prepare the impregnation solution. About 20 g of the support as in Comparative Example 1 was put into a 100 ml beaker, into which the prepared impregnation solution was added to impregnate the support. The impregnated support was dried at about 120° C. for about 8 h and decomposed in an air atmosphere at about 450° C. to yield catalyst 2-1. The SEM measurement shows that about 90% palladium and silver were distributed in the catalyst body within the thickness between the support surface and the depth of about 500–1000 μm.

Example 2

About 1.0 ml of silver nitrate containing about 10 mg Ag/ml, about 0.85 ml of palladium nitrate containing about 4.7 mg Pd/ml and about 5.5 ml of water were added into a beaker and thoroughly mixed. The pH value of the solution was adjusted to pH=1.2 with, such as nitric acid and ammonia, to prepare the impregnation solution. About 20 g of the support as in Comparative Example 1 was put into a 100 ml beaker, into which the prepared impregnation solution was added to impregnate the support. The impregnated support was dried at about 120° C. for about 8 h and decomposed in an air atmosphere at about 450° C. to yield catalyst 2-2. The SEM measurement shows that 90% palladium and silver were distributed in the catalyst body within the thickness between the support surface and the depth of about 500–1000 μm.

Example 3

About 3.9 ml of auric chloride containing about 4.8 mg Au/ml, about 0.85 ml of palladium nitrate containing about 4.7 mg Pd/ml and about 2.5 ml of water were added into a beaker and thoroughly mixed. The pH value of the solution was adjusted to pH=1.2 with, such as nitric acid and ammonia, to prepare the impregnation solution. About 20 g of the support as in Comparative Example 1 was put into a 100 ml beaker, into which the prepared impregnation solution was added to impregnate the support. The impregnated support was dried at about 120° C. for about 8 h and decomposed in an air atmosphere at about 450° C. to yield catalyst 2-3. The SEM measurement shows that 90% palladium and silver were distributed in the catalyst body within the thickness between the support surface and the depth of about 500–1000 μm.

Example 4

About 1.2 ml of silver nitrate containing about 5 mg Ag/ml, about 1.2 ml of palladium nitrate containing about 4.7 mg Pd/ml and about 5.0 ml of water were added into a beaker and thoroughly mixed. The pH value of the solution was adjusted to pH=1.2 with, such as nitric acid and ammonia, to prepare the impregnation solution. About 20 g of the support as in Comparative Example 1 was put into a 100 ml beaker, into which the prepared impregnation solution was added to impregnate the support. The impregnated support was dried at about 120° C. for about 8 h and decomposed in an air atmosphere at about 450° C. to yield catalyst 2-4. The SEM measurement shows that 90% palladium and silver were distributed in the catalyst body within the thickness between the support surface and the depth of about 500–1000 μm.

Example 5

About 6 ml of silver nitrate containing about 5 mg Ag/ml, about 1.2 ml of palladium nitrate containing about 4.7 mg Pd/ml were added into a beaker and thoroughly mixed. The pH value of the solution was adjusted to pH=1.2 with, such as nitric acid and ammonia, to prepare the impregnation solution. About 20 g of the support as in Comparative Example 1 was put into a 100 ml beaker, into which the prepared impregnation solution was added to impregnate the support. The impregnated support was dried at about 120° C. for about 8 h and decomposed in an air atmosphere at about 450° C. to yield catalyst 2-5. The SEM measurement shows that 90% palladium and silver were distributed in the catalyst body within the thickness between the support surface and the depth of about 500–1000 μm.

Example 6

$TiCl_4$ solution was neutralized with NaOH solution of the same equivalence as that of $TiCl_4$ at 40° C. to conduct co-precipitation, and then stirred for about 24 h to turn the resultant titanium hydroxide into uniform crystal particles. The suspension was filtered and washed away the $Na^+$ and $Cl^-$ ions with deionized distilled water and then the resultant hydroxide was dried at about 120° C. The dry sample was pulverized into fine powders of about 120–180 mesh. After kneading, it was extruded into long strips of about (p3 mm using such as a twin screw extruder. The strips were dried at about 120° C. and calcined in a muffle furnace at about 1100° C. for about 4 h to yield the required $TiO_2$ support having a bulk density of about 1.25 g/ml, a pore volume of about 0.17 ml/g, a specific surface area of about 4.9 m²/g (BET nitrogen method) or about 17.5 m²/g (mercury intrusion method), a most probable pore diameter of about 98 nm, and a mean pore diameter of about 51 nm.

About 1.0 ml of silver nitrate containing about 10 mg Ag/ml, about 0.85 ml of palladium nitrate containing about 4.7 mg Pd/ml and about 2.0 ml of water were added into a beaker and thoroughly mixed, then pH value of the solution was adjusted to pH 1.2 with, such as nitric acid and ammonia, to prepare the impregnation solution. About 20 g of the support was put into a 100 ml beaker, into which the impregnation solution was added to impregnate the support. The impregnated support was dried at about 120° C. for about 8 h and decomposed in an air atmosphere at about 450° C. to yield catalyst 2-6. The SEM measurement shows that 90% palladium and silver were distributed in the catalyst body within the thickness between the support surface and the depth of about 500–1000 μm.

Example 7

$NaAlO_2$ solution and $TiCl_4$ solution were mixed at about 40° C., then the mixture was neutralized with NaOH solution to form a co-precipitate of aluminum-titanium hydroxide, which was stirred for about 24 h to form uniform crystal particles. The resultant was filtered and washed away the $Na^+$ and $Cl^-$ ions with deionized distilled water and then the resultant mixed hydroxide was dried at about 120° C. The dry sample was pulverized into fine powders of about 120–180 mesh. After kneading, it was extruded into long strips of about (p3 mm, such as using a twin screw extruder. After being dried at about 120° C., the strips were calcined in a muffle furnace at about 900° C. for about 2 h to yield an alumina-titania mixed support ($Al_2O_3/TiO_2$=:1) having a bulk density of about 0.8 g/ml, a pore volume of about 0.4 ml/g, a specific surface area of about 22.1 m²/g (BET nitrogen method) or about 36.6 m²/g (mercury intrusion method). The support exhibited a two peaks distribution at about 50 nm and about 1000 nm and the mean pore diameter was about 58 nm.

About 1.0 ml of silver nitrate containing about 10 mg Ag/ml, about 0.85 ml of palladium nitrate containing about 4.7 mg Pd/ml and about 6.1 ml of water were added into a beaker and thoroughly mixed. The pH value of the solution was adjusted to pH=1.2 with, such as nitric acid and ammonia, to prepare the impregnation solution. About 20 g of the support was put into a 100 ml beaker, into which the impregnation solution was added to impregnate the support. The impregnated support was dried at about 120° C. for about 8 h and decomposed in an air atmosphere at about 450° C. to yield catalyst 2-7. The SEM measurement shows that 90% palladium and silver were distributed in the catalyst body within the thickness between the support surface and the depth of about 500–1000 μm.

Example 8

About 0.8 ml of each catalyst prepared in the above examples was loaded into an isothermal reactor with a loading diameter of about 5 mm and a loading height of about 40 mm. The composition of the feed is shown in Table 1. Selective hydrogenation was conducted under a reaction pressure of about 1.6 MPa and a space velocity of about 10000 h⁻¹. Table 2 presents the temperature, selectivity for acetylene hydrogenation and conversion of propyne and propadiene (MAPD) corresponding to an exit acetylene concentration less than about 1 ppm.

The selectivity for acetylene hydrogenation (abbreviated as selec.) and the conversion of MAPD (abbreviated as conv.) are important indices reflecting the activity and selectivity of the catalyst, and the formula for their calculation are as follows:

$$\text{Selec.} = \frac{C_2H_4 \text{ conc.(mol \%) after reaction} - C_2H_4 \text{ conc.(mol \%) before reaction}}{C_2H_2 \text{ conc.(mol \%) before reaction} - C_2H_2 \text{ conc.(mol \%) after reaction}} \times 100\%$$

$$\text{Conv.} = \frac{MADP \text{ conc.(mol \%) before reaction} - MADP \text{ conc.(mol \%) after reaction}}{MADP \text{ conc.(mol \%) before reaction}} \times 100\%$$

TABLE 1

| | Composition of the Feed Gas | | | | | | | |
|---|---|---|---|---|---|---|---|---|
| Component | $H_2$ | $C_2H_6$ | $C_2H_4$ | $C_2H_2$ | $C_3H_8$ | $C_3H_6$ | MAPD | CO |
| Content (mol %) | 15–45 | 8–12 | 30–50 | 0.3–0.7 | 0.8–1.5 | 10–20 | 0.4–0.8 | 0.01–1.0 |

TABLE 2

Reaction Results of the Catalyst

| | Catalyst No. | | | | | | | | |
|---|---|---|---|---|---|---|---|---|---|
| | 1-1 | 1-2 | 2-1 | 2-2 | 2-3 | 2-4 | 2-5 | 2-6 | 2-7 |
| Distribution of active component ($\mu$m) | <300 | <300 | <500–1000 | <500–1000 | <500–1000 | <500–1000 | <500–1000 | <500–1000 | <500–1000 |
| Active component | Pd | Pd/Ag | Pd/Cu | Pd/Ag | Pd/Au | Pd/Ag | Pd/Ag | Pd/Ag | Pd/Ag |
| Inlet hydrogen (mol %) | 43.4 | 27.1 | 43.4 | 43.4 | 43.4 | 27.1 | 27.1 | 26.1 | 26.1 |
| CO content (ppm) | 1600 | 2400 | 2400 | 1600 | 1600 | 2400 | 2400 | 1400 | 1400 |
| Inlet $C_2H_2$ (mol %) | 0.42 | 0.43 | 0.42 | 0.42 | 0.42 | 0.43 | 0.43 | 0.50 | 0.50 |
| Inlet MAPD (mol %) | 0.45 | 0.51 | 0.45 | 0.45 | 0.45 | 0.51 | 0.51 | 0.60 | 0.60 |
| Reaction Tem. (° C.) | 82.5 | 90 | 80 | 90 | 80 | 85 | 95 | 80 | 85 |
| Selec. (%) | 1.5 | 12.2 | 39.4 | 64.2 | 21.4 | 49.5 | 50.3 | 70.2 | 36.3 |
| Conv. (%) | 72.9 | 65.4 | 62.3 | 68.1 | 71.8 | 67.5 | 62.2 | 58.8 | 71.3 |

Table 2 shows that the catalysts of the present invention all have higher selectivity for acetylene hydrogenation into ethylene and higher MAPD conversion at various concentrations of hydrogen and CO. At higher hydrogen content, the catalyst containing only active component palladium has very low selectivity for acetylene hydrogenation into ethylene (only 1.5%) and very low MAPD conversion, while under the identical reaction conditions, the selectivity of the Pd/Ag catalyst of the present invention is about 64.2% and the selectivity of the Pd/Au catalyst of the present invention is about 21.4%. Under the identical reaction conditions, the selectivity of the catalyst wherein palladium is distributed in shell and silver is distributed in bulk is about 12.2%, while the selectivity of the catalysts of the present invention is about 49.5% and about 49.3%, respectively.

Example 9

The activity for the selective hydrogenation of alkynes and dienes over catalyst 2-2 was examined using a series of two adiabatic reactors with a cooler in between. Each reactor was made from stainless steel of about 25 mm i.d., the upper part of which was the preheating section and the lower part was the catalyst bed. The catalyst loading of each reactor was about 200 ml. The height of the catalyst bed was about 400 mm. The conversion of acetylene in the first reactor was controlled to be about 90%. The results are shown in Table 3.

TABLE 3

Reaction Results in the Two Reactor Systems

| | Space velocity ($h^{-1}$) | | | | | | |
|---|---|---|---|---|---|---|---|
| | 8000 | | | 12000 | | | |
| | Reaction pressure (MPa) | | | | | | |
| | 3.70 | 3.50 | 3.50 | 3.5 | 3.48 | 3.52 | 3.42 |
| | CO conc. (ppm) | | | | | | |
| | 816 | 560 | 630 | 683 | 762 | 955 | 765 |
| Reactor 1 | | | | | | | |
| Inlet $H_2$ (mol %) | 15.18 | 15.14 | 9.90 | 20.43 | 17.86 | 18.30 | 20.21 |
| Inlet $C_2H_2$ (mol %) | 0.694 | 0.646 | 0.709 | 0.628 | 0.600 | 0.630 | 0.584 |

TABLE 3-continued

Reaction Results in the Two Reactor Systems

| | Space velocity ($h^{-1}$) | | | | | | |
|---|---|---|---|---|---|---|---|
| | 8000 | | | 12000 | | | |
| | Reaction pressure (MPa) | | | | | | |
| | 3.70 | 3.50 | 3.50 | 3.5 | 3.48 | 3.52 | 3.42 |
| | CO conc. (ppm) | | | | | | |
| | 816 | 560 | 630 | 683 | 762 | 955 | 765 |
| Exit $C_2H_2$ (mol %) | 0.110 | 0.047 | 0.042 | 0.065 | 0.052 | 0.081 | 0.034 |
| Inlet MAPD (mol %) | 0.437 | 0.448 | 0.523 | 0.459 | 0.444 | 0.439 | 0.444 |
| Inlet Temp. (° C.) | 52.8 | 57.2 | 59.8 | 62.7 | 66.3 | 66.1 | 66.2 |
| Exit Temp. (° C.) | 71.7 | 81.8 | 82.16 | 89.0 | 89.1 | 89.3 | 89.9 |
| Reactor 2 | | | | | | | |
| Inlet Temp. (° C.) | 56.4 | 65.2 | 67.7 | 71.6 | 76.4 | 76.5 | 79.8 |
| Exit Temp. (° C.) | 69.3 | 87.4 | 87.5 | 93.0 | 96.8 | 95.8 | 96.2 |
| Exit $C_2H_2$ (ppm) | <1 | <1 | <1 | <1 | <1 | <1 | <1 |
| Total conv. of $C_2H_2$ (%) | 100 | 100 | 100 | 100 | 100 | 100 | 100 |
| Selec. (%) | 74.97 | 69.95 | 76.27 | 77.34 | 68.95 | 71.76 | 75.14 |
| Conv. (%) | 47.18 | 52.46 | 53.36 | 53.90 | 57.67 | 52.99 | 56.11 |

Example 10

Catalyst 1-4 and 2-2 were loaded in two parallel reactors and the relation of their activity and selectivity with time on stream (TOS) was determined under the identical reaction conditions, such as shown in FIG. 1. Each reactor was made from stainless steel of about 25 mm i.d., the upper part of which was the preheating section and the lower part was the catalyst bed. Heating wire was wrapped around the outer wall to heat the reactor or maintain its temperature. The loading of each reactor was about 200 ml. The height of the catalyst bed was about 400 mm.

Catalyst 1-4 was a commercial $Pd/Ag/Al_2O_3$ catalyst containing about 0.024 wt % Pd and about 0.068 wt % Ag with the other being alumina. The catalyst was prepared completely according to the process, such as disclosed in U.S. Pat. No. 4,404,124. Pd was distributed in the shell of about 300 $\mu$m in thickness and Ag in the bulk. The catalyst was provided by Nissan Girdler Catalyst Co. Ltd. and had a tradename of G-83C.

The catalysts had not been reduced and the reactant feed was directly introduced to effect the reaction. During the about 0–250 h of TOS, the space velocity was about 8000 $h^{-1}$. During about 250–560 h of TOS, the space velocity was about 12000 $h^{-1}$. At the inlet, the concentration of acetylene was about 0.6–0.7 mol %. The concentration of hydrogen was about 10–20 mol %. The concentration of CO was about 600–1000 ppm. The reaction temperature was about 60–120° C. The reaction pressure was about 3.6 MPa.

After near 600 h of TOS, the weight of Catalyst 1-4 increased by about 19.1 g, and that of Catalyst 2-2 increased by about 16.7 g, showing that the yield of the green oil on the catalyst of the present invention was lower. FIG. 1 shows that the conversions of acetylene and MAPD on the catalyst of the present invention maintained basically constant during the about 600 h of TOS and the selectivity for the acetylene hydrogenation into ethylene was always higher than that of Catalyst 1-3, while the conversions of acetylene and MAPD on the comparative catalyst started to drop at about 380 h. This demonstrates that the uniform distribution of the active components palladium and silver increases the selectivity of the catalyst and the suitably deep distribution of the active components increases the activity of the catalyst, decreases the yield of the green oil, and improve the stability of the catalyst.

Example 11

The support derived in Comparative Example 1 was impregnated using the same method as in Comparative Example 2 to yield Catalyst 1-3 with the exception that the support was impregnated after the pH value of the impregnation solution had been adjusted to be about 5. The distribution of the metals in the catalyst was determined with SEM and the result showed that about 90% Pd and Ag were distributed in the shell of about 300 μm in thickness.

About 0.8 ml of the catalyst was loaded into an isothermal reactor to form a bed of about 5 mm in diameter and about 40 mm in length. The composition of the feed as shown in Table 4. The pressure of the feed stream was about 1.6 MPa and the space velocity was about 10000 $h^{-1}$. The results of the selective hydrogenation were shown in Table 5.

TABLE 4

Composition of the Reaction Feed

| Component | $H_2$ | $CH_4$ | $C_2H_6$ | $C_2H_4$ | $C_2H_2$ | $C_3H_8$ | $C_3H_6$ | MAPD | CO |
|---|---|---|---|---|---|---|---|---|---|
| Content (mol %) | 18.56 | 0.06 | 10.38 | 51.54 | 0.31 | 0.71 | 17.63 | 0.49 | 0.08 |

TABLE 5

Relation of Hydrogenation Activity and Selectivity for Acetylene Hydrogenation into Ethylene of the Catalyst with Reaction Temperature

| Temp. (° C.) | Concentration of $C_2H_2$ at outlet (ppm) | Selectivity to $C_2H_4$ (%) | Conversion of MAPD (%) |
|---|---|---|---|
| 80 | 1700 | 64.4 | 9.8 |
| 90 | 510 | 76.1 | 20.7 |
| 100 | 24 | 60.6 | 57.7 |
| 110 | <1 | −158.4 | 83.7 |

Example 12

About 0.8 ml of Catalyst 2-2 was loaded into an isothermal reactor to form a bed of about 5 mm in diameter and about 40 mm in height. The composition of the feed is shown in Table 6. The pressure of the feed stream was about 1.6 MPa and the space velocity was about 10000 $h^{-1}$. The results of the selective hydrogenation are shown in Table 7.

TABLE 6

Composition of the Reaction Feed

| Component | $H_2$ | $C_2H_6$ | $C_2H_4$ | $C_2H_2$ | $C_3H_8$ | $C_3H_6$ | MAPD | CO |
|---|---|---|---|---|---|---|---|---|
| Content (mol %) | 22.73 | 9.62 | 52.70 | 0.53 | 0.53 | 13.42 | 0.39 | 0.08 |

TABLE 7

Relation of Hydrogenation Activity and Selectivity for Acetylene Hydrogenation into Ethylene of the Catalyst with Reaction Temperature

| Temp. (° C.) | Concentration of $C_2H_2$ at outlet (ppm) | Selectivity to $C_2H_4$ (%) | Conversion of MAPD (%) |
|---|---|---|---|
| 70 | 980 | 82.9 | 19.6 |
| 75 | 81 | 84.5 | 34.9 |
| 80 | 2.1 | 87.7 | 57.3 |
| 85 | <1 | 76.3 | 61.2 |
| 90 | <1 | 59.8 | 69.3 |

It can be seen from the above results that the catalyst of the present invention can attain higher acetylene conversion, higher selectivity for acetylene hydrogenation into ethylene, and higher MAPD conversion at low temperatures compared to the catalyst wherein the active components are distributed within the shell of thickness between the support surface and the depth of less than about 300 μm, therefore it has higher activity.

What is claimed is:

1. A selective hydrogenation catalyst comprising:
   an inorganic oxide support selected from the group consisting of alumina, titania, and a chemical composite of alumina and titania;
   a major active component palladium of a content of about 0.002–1.0% based on the total weight of the catalyst; and
   at least one promoter selected from Group IB metals, the mole ratio of palladium to the Group IB metal is in the range of about 1 to about 20;
   wherein the major component palladium and the promoter are uniformly distributed together in the catalyst within the thickness between the support surface and the depth of more than about 300 μm.

2. The catalyst according to claim 1, wherein the content of alumina in the chemical composite of alumina and titania is about 1–99% by weight.

3. The catalyst according to claim 2, wherein the content of alumina is about 20–80% by weight.

4. The catalyst according to claim 3, wherein the content of alumina is about 40–60% by weight.

5. The catalyst according to claim 4, wherein the support comprises the following physical properties: bulk density of about 0.7–0.9 g/ml, pore volume of about 0.3–0.6 ml/g, specific surface area of about 10–60 m$^2$/g, mean pore diameter of about 40–100 nm.

6. The catalyst according to claim 1, wherein the content of the major active component palladium is about 0.005–0.5 wt %.

7. The catalyst according to claim 6, wherein the content of the major active component palladium is about 0.01–0.05 wt %.

8. The catalyst according to claim 1, wherein the promoter is selected from the group consisting of Cu, Ag, and Au.

9. The catalyst according to claim 1, wherein the mole ratio of palladium to the Group IB metal is in the range of about 1–10.

10. The catalyst according to claim 9, wherein the mole ratio of palladium to the Group IB metal is in the range of about 1.0–5.0.

11. The catalyst according to claim 1, wherein the active component palladium and the promoter Group IB metal existing in the form of oxides in the support are reduced to fine alloy particles with a diameter of about 2–10 nm.

12. The catalyst according to claim 1, wherein the dispersion depth is within the thickness between the support surface and the depth of 500–1000 μm.

13. The catalyst according to claim 1, further comprising alkali metals and/or alkaline earth metals.

* * * * *